United States Patent
Bajor et al.

(10) Patent No.: US 6,599,936 B1
(45) Date of Patent: Jul. 29, 2003

(54) ANTI-SEBUM SKIN CARE COSMETIC COMPOSITIONS CONTAINING BRANCHED ESTERS

(75) Inventors: John Bajor, Ramsey, NJ (US); Stephan Samuel Habif, Demarest, NJ (US); Laura Rose Palanker, Jackson, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 12 days.

(21) Appl. No.: 09/585,010

(22) Filed: Jun. 1, 2000

Related U.S. Application Data

(60) Provisional application No. 60/137,317, filed on Jun. 3, 1999.

(51) Int. Cl.$^7$ .................. A01N 47/40; A01N 37/00; A01N 37/02; A01N 37/06; A01N 25/00; A61K 7/00; A61K 7/44

(52) U.S. Cl. .................. 514/532; 514/506; 514/529; 514/546; 514/549; 514/846; 514/873; 424/401; 424/60

(58) Field of Search .................. 424/401, 60; 514/506, 514/846, 873, 529, 532, 546, 549

(56) References Cited

U.S. PATENT DOCUMENTS

| | | | | |
|---|---|---|---|---|
| 4,323,694 A | * | 4/1982 | Scala, Jr. ................ 560/103 |
| 4,496,536 A | | 1/1985 | Moller et al. ................ 424/70 |
| 4,772,522 A | * | 9/1988 | Kubota et al. ............ 252/62.54 |
| 5,063,057 A | | 11/1991 | Spellman et al. ........... 424/401 |
| 5,093,112 A | | 3/1992 | Birtwistle et al. ............ 424/70 |
| 5,318,954 A | * | 6/1994 | Mueller et al. ............. 507/138 |
| 5,344,850 A | | 9/1994 | Hata et al. .................. 514/739 |
| 5,489,426 A | | 2/1996 | Zabotto et al. ............... 424/59 |
| 5,571,503 A | * | 11/1996 | Mausner ...................... 424/59 |
| 5,578,299 A | | 11/1996 | Starch ..................... 424/78.03 |
| 5,593,691 A | | 1/1997 | Eugster et al. ............. 424/461 |
| 5,658,580 A | | 8/1997 | Mausner ..................... 424/401 |
| 5,720,961 A | * | 2/1998 | Fowler et al. .............. 424/401 |
| 5,773,015 A | | 6/1998 | Bajor et al. ................ 424/401 |
| 5,811,110 A | * | 9/1998 | Granger et al. ............. 424/401 |
| 5,849,273 A | | 12/1998 | Bonda et al. ................. 424/59 |
| 5,863,461 A | * | 1/1999 | Ansmann et al. ........... 424/401 |
| 5,968,528 A | * | 10/1999 | Deckner et al. ............ 424/401 |
| 6,001,377 A | * | 12/1999 | SaNogueira, Jr. et al. .. 424/401 |

FOREIGN PATENT DOCUMENTS

| | | |
|---|---|---|
| CH | 683426 | 3/1994 |
| EP | 596 284 | 5/1994 |
| WO | 95/00107 | 1/1995 |
| WO | WO 97/39060 | * 10/1997 |

OTHER PUBLICATIONS

PCT International Search Report in a PCT application PCT/EP 00/04749, Oct. 2000.

* cited by examiner

*Primary Examiner*—Sreeni Padmanabhan
*Assistant Examiner*—Michael A. Willis
(74) *Attorney, Agent, or Firm*—Ellen Plotkin

(57) ABSTRACT

Cosmetic skin care methods and compositions containing methyl-branched esters. The inventive compositions provide control of sebum secretion from sebocytes, improved oil control and improved skin feel, prevent shine and stickiness, while also. providing anti-aging benefits which results in reduced appearance of wrinkles and aged skin, improved skin color, treatment of photoaged skin, improvement in skin's radiance and clarity and finish, and an overall healthy and youthful appearance of the skin.

2 Claims, No Drawings

ANTI-SEBUM SKIN CARE COSMETIC COMPOSITIONS CONTAINING BRANCHED ESTERS

This Application claims priority from a Provisional Application Ser. No. 60/137,317 filed Jun. 3,1999.

FIELD OF THE INVENTION

Cosmetic skin care compositions containing branched esters for controlling sebum/oil on human skin and improving or preventing the appearance of aged skin.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. Consumers also seek other benefits in addition to anti-aging.

A frequent, undesirable skin condition is "oily skin," the condition which results from the excessive amount of sebum on the skin. Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups. Cosmetic products which provide both sebum control and anti-aging benefits are highly desirable.

Several patents disclose the use of branched alcohols in cosmetic compositions. See for instance U.S. Pat. No. 4,496,536 (Moller et al.), U.S. Pat. No. 5,093,112 (Birtwistle et al.), and U.S. Pat. No. 5,344,850 (Hata et al.).

Unfortunately, alcohols, whether branched or not, have a sharp unpleasant odor and thus present a formulation challenge for a cosmetic chemist. The esterification of alcohols changes their odor, but not necessarily for the better.

Cosmetic compositions containing branched esters are also known. U.S. Pat. No. 5,489,426 (Zabotto et al.) describes cosmetic composition containing branched alkyl esters, wherein the branched hydrocarbon chain contains from 3 to 20 carbon atoms. U.S. Pat. No. 5,578,299 (Starch) describes cosmetic rinse-off compositions containing 49–98% of mineral oil and, optionally, a branched chain alcohol ester as an emollient. U.S. Pat. No. 5,658,580 (Mausner) describes anti-sebum compositions containing selected neopentanoate esters to smooth the skin. U.S. Pat. No. 5,773,015 (Bajor et al.) describes anti-sebum compositions containing C11–C30 esters of salicylic acid. U.S. Pat. No. 5,849,273 (Bonda et al.) describes a sunscreen composition containing an alkyl salicylate ester and, optionally, an alkyl benzoate ester; both esters contain a single-branched alkyl, the branch consisting of butyl, or hexyl or octanoyl alkyl radical.

The present invention is based, at least in part, on the discovery of branched esters that have a pleasant scent and also are effective sebum suppressors. It has been iscovered, as part of the present invention that esters of straight chain alcohols are not effective and that not all branched chain alcohol esters are either effective or have a pleasant scent.

SUMMARY OF THE INVENTION

The present invention includes a skin care cosmetic composition comprising:

(i) from about 0.001% to about 50% of a branched chain ester RCOOR', wherein R is selected from the group consisting of $CH_3$, phenyl, and $CH_3(CH_2)_4CH=CHCH_2CH=CH(CH_2)_7$; and R' is a methyl-branched hydrocarbon radical containing a total of at least 6 carbons, provided that if R' contains more than 6 carbons total, the branched ester contains more than one methyl group; and (ii) a cosmetically acceptable vehicle.

The present invention also includes a method of controlling or preventing an oily skin condition, especially in the facial area, by applying to the skin a composition from about 0.001% to about 100% of the branched ester as described above.

The invention also includes a cosmetic method of reducing, preventing or controlling sebum secretion from sebocytes by applying a composition comprising from about 0.001% to about 100% of the branched ester.

The invention also includes a cosmetic method of stimulating collagen and glycosaminoglycan synthesis by fibroblasts in the skin, by applying a composition comprising from about 0.001% to about 100% of the branched ester.

The invention also includes a cosmetic method of treating or delaying chronoaged, photoaged, dry, lined or wrinkled skin, shielding the skin from harmful UVA and UVB light (sunscreening), increasing stratum corneum firmness and flexibility, and generally increasing the quality of skin by applying to the skin the inventive composition.

The inventive methods and compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, hands and scalp.

The inventive methods and compositions include a branched chain ester RCOOR' wherein R is selected from the group consisting of: (acetate esters), phenyl (benzoate esters), and $CH_3(CH_2)_4CH=CHCH_2CH=CH(CH_2)_7$ (linoleate esters); and R' is a branched aliphatic hydrocarbon radical containing a total of at least 6 carbon atoms and containing solely methyl branches, provided that if R' contains more than 6 carbons total, the branched ester contains more than 1 methyl group.

Preferably R' contains from 6 to 20 carbons, most preferably from 10 to 13 carbons, to attain optimum efficacy. The preferred esters are selected from linoleate esters due to their optimum performance.

The alcohol, which serves as a starting material for the ester, may contain a mix of various chain lengths' alcohols and various branches. Such mixed alcohol is suitable for use in the present invention, as long as the predominant alcohol in the mix contains a total of at least 6 carbon atoms and methyl branching The ester is employed in the inventive methods in an amount of from 0.001% to about 100%, preferably from 0.1% to 20%, most preferably from 0.1% to 10%.

The branched esters within the scope of the invention are commercially available, e.g. from Exxon (under Exxate® trademark) or may be synthesized in accordance with the procedures in Example 1.

The preferred inventive compositions and methods also include an oil-absorbing powder. Examples of suitable oil-absorbing powder include but are not limited to silica (preferably fumed), talcum, and clay. The preferred oil-absorbing powder is fumed silica, due to its superior oil-absorbing capacity.

The oil-absorbing powder provides an immediate sebum control, but not a long-term relief, since it cannot be used in large amounts without whitening the skin. According to the present invention, the oil-absorbing powder may be present in an amount of no greater than 1%, generally from 0.01% to 1%, preferably from 0.1% to 1%, most preferably from 0.5% to 1%.

Although the branched esters employed in the inventive methods and compositions are liquid, and thus the invention is effective even in the absence of the carrier, the compositions according to the invention comprise a cosmetically acceptable vehicle to act as a diluant, dispersant or carrier for branched ester so as to facilitate their distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, pplyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients and sunscreens.

Preferred additional anti-sebum ingredient is a retinoid. The term "retinoids" as used herein includes retinoic acid, retinol, retinal and retinyl esters.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl esters suitable for use in the present invention are C1–C30 esters of retinol, preferably C2–C20 esters, and most preferably C2, C3, and C16 esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

A retinoid may be present in the inventive compositions in an amount 33 to 330,000 IU per gram of the composition, preferably 330 to 16,500 IU, most preferably 1,650 to 6,600 IU.

The inventive compositions are preferably essentially free of mineral oil, since the ability of the inventive composition to control sebum production would be decreased or eliminated in the presence of mineral oil.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy4-methoxy benzophenone (also known as oxybenzone) can be used. Octyl methoxycinnamate and 2-hydroxy4-methoxy benzophenone are commercially available is under the trademarks Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

The composition according to the invention is intended primarily as a product for topical application to human skin, especially as an agent for controlling or preventing excessive sebum secretion.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

EXAMPLE 1

This example describes the synthesis of the following isotridecyl esters: butyrate, nonanoate, decanoate, benzoate, and linoleate.

Esters were synthesized via an alcoholysis reaction of the corresponding acid chloride (e.g. butyric acid chloride) and iso-tridecanol (Exxal® 13).

The following acid chlorides were purchased from Nu-Chek-Prep, Inc. and used as is: Linoleoyl. The following acid chlorides were purchased from Aldrich: Benzoyl and butyryl. The following acid chlorides were synthesized: Salicoyl, nonanoyl, decanoyl Into a clean, dry 250 mL round bottomed flask were added 1.0 equivalents of acid, 100 mLs of anhydrous methylene chloride and a few drops of pyridine. The flask was equipped with a stir bar, addition funnel and nitrogen bubbler. To the addition funnel were added 1.05 equivalents of thionyl chloride dissolved in ~20 mLs of methylene chloride. The thionyl chloride solution was added dropwise to the reaction mixture at ambient temperature. When the addition was complete, the reaction mixture was heated to 45–50° C. for two hours before the heat was removed and the reaction cooled to room temperature. The majority of methylene chloride, as well as excess thionyl chloride, was removed under reduced pressure.

Synthesis of Isotridecyl Esters

Into a clean, dry 250 mL round bottomed flask were added 1.0 equivalents of Exxal® 13 (from Exxon Chemical Co.), 100 mLs of anhydrous methylene chloride and 1.0 equivalents of anhydrous pyridine. The flask was equipped with a stir bar, addition funnel and nitrogen bubbler. To the addition funnel was added the acid chloride solution from the previous step. The acid chloride solution was added dropwise to the reaction mixture at ambient temperature. When the addition was complete, the reaction mixture was heated to 45–50° C. for two hours before the heat was removed and the reaction cooled to room temperature. The crude product was then purified by column chromatography.

Isotridecyl Benzoate: Product is the result of alcoholysis reaction of benzoyl chloride and iso-tridecanol (Exxal® 13). The crude product was purified by column chromatography. Purity 98% by gas chromatography.

Isotridecyl Butyrate: Product is the result of alcoholysis reaction of butyryl chloride and iso-tridecanol (Exxal® 13): Product was purified by column chromatography. Aliphatic chain is mixture of many branched isomers. Purity 99% by gas chromatography.

Isotridecyl Decanoate: Product is the result of alcoholysis reaction of decanoyl chloride and iso-tridecanol (Exxal® 13). Product was purified by column chromatography. Aliphatic chain is mixture of many branched isomers. Purity 99% by gas chromatography.

Isotridecyl Linoleate: Product is the result of alcoholysis reaction of linoleoyl chloride and iso-tridecanol (Exxal® 13). The crude product was purified by column chromatography. Purity 98% by gas chromatography.

Isotridecyl Nonanoate: Product is the result of alcoholysis reaction of nonanoyl chloride and iso-tridecanol (Exxal® 13). Product was purified by column chromatography. Aliphatic chain is mixture of many branched isomers. Purity 99% by gas chromatography.

EXAMPLE 2

This example measured sebum suppression by various acetate branched esters in vitro.

The Exxate® esters used in the Examples were obtained from Exxon and are as follows:

| Trade Name | Branching |
| --- | --- |
| Exxate ® 600 | Acetate ester of methyl branched 1-pentanols |
| Exxate ® 700 | Acetate ester of Exxal ® 7, which is a mixture of branched and straight chain isomers, about 40% dimethyl pentanols. |
| Exxate ® 800 | Acetate ester of Exxal ® 8, which is dimethyl hexanols. |
| Exxate ® 900 | Acetate ester of Exxal ® 9, which is dimethyl heptanols |
| Exxate ® 1000 | Acetate ester of Exxal ® 10, which is trimethyl heptanols and dimethyl octanols |
| Exxate ® 1200 | Acetate ester of Exxal ® 12, which is trimethyl nonanols |
| Exxate ® 1300 | Acetate ester of Exxal ® 13, which is tetramethyl nonanols and trimethyl decanols |

Sebocyte Assay Procedure

Secondary cultures of human sebocytes obtained from an adult male were grown in 48-well or 96-well tissue culture plates (Costar Corp.; Cambridge, Mass.) until three days post-confluence. Sebocyte growth medium consisted of Clonetics Keratinocyte Basal Medium (KBM) supplemented With 14 µg/ml bovine pituitary extract, 0.4 µ/ml hydrocortisone, 5 µ/ml insulin, 10ng/ml epidermal growth factor, $1.2 \times 10^{-10}$ M cholera toxin, 100 units/ml penicillin, and 100 µg/ml streptomycin. All cultures were incubated at 37° C. in the presence of 7.5% $CO_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (triplicates) with 1–5 microliter of test agent solubilized in ethanol. Controls consisted of addition of ethanol alone. Each plate was returned to the incubator for 20 hours followed by the addition of $^{14}$C-acetate buffer (5 mM final concentration, 56 mCi/mmol specific activity). Sebocytes were returned to the incubator for four hours afterwhich each culture was rinsed three times with phosphate buffered saline to remove unbound label. Radioactive label remaining in the sebocytes was harvested and counted using a Beckman scintillation counter. Statistical significance (p value) was calculated using student's t-test. The results that were obtained are summarized in Tables 1 and 2. Phenol Red, a known sebum suppressive agent, was employed as a positive control.

TABLE 1

| 20 hour Incubation, 48 well plate | | | |
| --- | --- | --- | --- |
| Treatment | % Reduction | Std Deviation | P value |
| 0.001% Phenol Red | 19.6 | 4.3 | 0.043 |
| 0.001% Exxate ® 600 | 23.3 | 7.8 | 0.03 |
| 0.01% Exxate ® 600 | 39.0 | 13.6 | 0.008 |
| 0.001% Exxate ® 700 | 46.1 | 11.4 | 0.03 |
| 0.01% Exxate ® 700 | 47.0 | 11.1 | 0.002 |
| 0.001% Exxate ® 800 | 29.5 | 10.5 | 0.017 |
| 0.01% Exxate ® 800 | 42.4 | 9.6 | 0.003 |
| 0.001% Exxate ® 900 | 21.3 | 12.4 | 0.03 |
| 0.01% Exxate ® 900 | 23.0 | 2.3 | 0.002 |
| 0.001% Exxate ® 1000 | 27.1 | 6.1 | 0.002 |
| 0.01% Exxate ® 1000 | 22.8 | 12.0 | 0.022 |
| 0.001% Exxate ® 1200 | 1.1 | 6.4 | 0.85 |
| 0.01% Exxate ® 1200 | 7.0 | 5.7 | 0.23 |
| 0.001% Exxate ® 1300 | 22.2 | 8.3 | 0.002 |
| 0.01% Exxate ® 1300 | 33.3 | 3.4 | 0.0001 |

The poor response in Exxate® 12 was unexpected because other Exxates were active; may be due to incorrect dilution of Exxate® from stock solution, prompted a re-evaluation of Exxates 9, 10, 12, 13

TABLE 2

| 20 hour Incubation, 48 well plate | | | |
| --- | --- | --- | --- |
| Treatment | % Reduction | Std Deviation | T-test |
| 0.001% Exxate ® 900 | 11.9 | 10.2 | .120 |
| 0.01% Exxate ® 900 | 31.2 | 20.2 | .057 |
| 0.001% Exxate ® 1000 | 28.4 | 12.0 | .016 |
| 0.01% Exxate ® 1000 | 42.1 | 11.4 | .003 |
| 0.001% Exxate ® 1200 | 20.3 | 4.1 | .108 |
| 0.01% Exxate ® 1200 | 38.2 | 8.2 | .023 |
| 0.001% Exxate ® 1300 | 21.9 | 3.5 | .089 |
| 0.01% Exxate ® 1300 | 42.6 | 14.7 | .029 |

The results in Tables 1 and 2 demonstrate that methyl-branched acetate esters (all within the scope of the invention) are effective sebum suppressors. All esters except Exxate® 600 had more than one methyl branch.

COMPARATIVE EXAMPLE 3

The sebocyte assay procedure described in Example 2 was repeated with additional branched esters. Isopropyl myristate was obtained from Sigma Chemical Co. Isotridecyl nonanoate, isotridecyl butyrate and isotridecyl decanoate were synthesised as described in Example 1. The results that were obtained are summarized in Table 3A–3C. Phenol Red was included as a positive control.

TABLE 3A 20 hour incubation, 96 well plate

| Treatment | % Reduction | Std Deviation | P value |
|---|---|---|---|
| 0.001% Phenol Red | 14.0 | 18.7 | 0.22 |
| 0.01% Phenol Red | 71.2 | 3.0 | 4.2e-06 |
| 0.001% Isopropyl Myristate | −6.3 | 8.3 | 0.33 |
| 0.01% Isopropyl Myristate | 4.0 | 3.0 | 0.41 |

The results in Table 3A demonstrate that a common emollient ester used in cosmetic compositions (isopropyl myristate) was not an effective sebum suppressor.

TABLE 3B 20 hour incubation, 48 well plate

| Treatment | % Reduction | T-test |
|---|---|---|
| 0.001% Isotridecyl Nonanoate | 0.7 | 0.90 |
| 0.01% Isotridecyl Nonanoate | (0.3) | 0.95 |
| 0.1% Isotridecyl Nonanoate | 0.8 | 0.85 |
| 0.001% Isotridecyl Decanoate | (11.9) | 0.05 |
| 0.01% Isotridecyl Decanoate | (6.5) | 0.38 |
| 0.1% Isotridecyl Decanoate | (9.3) | 0.26 |

TABLE 3C 20 hour incubation, 48 well plate

| Treatment | % Reduction | T-test |
|---|---|---|
| 0.000027% Isotridecyl Butyrate | (1.7) | 0.87 |
| 0.00027% Isotridecyl Butyrate | 4.1 | 0.66 |
| 0.0027% Isotridecyl Butyrate | 17.2 | 0.066 |

The results in Tables 3B and 3C demonstrate that isotridecyl nonanoate, isotridecyl decanoate and isotridecyl butyrate are not effective sebum suppressive agents.

COMPARATIVE EXAMPLE 4

The sebocyte assay procedure described in Example 2 was repeated with additional esters. The results that were obtained are summarized in Table 4. Isotridecyl salicylate (salicylate ester of Exxal® 13: a mixture of trimethyl and tetramethyl tridecanol) was obtained from Alzo Inc, 650 Jernee Mill Road Sayreville, N.J. 08872 and was included as an internal positive control. Straight chain TDS (tridecyl salicylate without branching), methyl TDS (salicylate ester of single methyl-branched tridecanol) and ethyl TDS (salicylate ester of single ethyl-branched tridecanol) were synthesised as follows:

General Procedure for the Synthesis of Alkyl Esters of Salicylic Acid

The alcohols used were as follows:
For:
   isotridecyl salicylate (branched): Exxal® 13
   straight chain TDS: 1-tridecanol (Aldrich)
   ethyl TDS: 3-hydroxy tridecanol (Lancaster)
   methyl TDS: 2-hydroxy tridecanol (Lancaster)

Step 1: Synthesis of Salicyloyl Chloride

Into a clean, dry three necked round bottomed flask were charged one equivalent of salicylic acid, 50 mls is of anhydrous toluene and a few drops of pyridine catalyst. The flask was equipped with a stir bar, thermometer and an addition funnel. Into the addition funnel was charged one equivalent of thionyl chloride in a few mls of toluene. The contents of the reaction flask were heated to 40° C. under a nitrogen blanket before the thionyl chloride solution was added slowly. Once the addition was complete, the reaction proceeded at 40–45° C. for several hours or until the reaction mixture was homogeneous. Upon completion of the reaction, any unreacted thionyl chloride was removed under vacuum.

Step 2: Synthesis of Ester

Into a clean, dry three necked round bottomed flask were charged one equivalent of alcohol, one equivalent of pyridine and 50 mls of anhydrous toluene. The flask was equipped with a stir bar, thermometer and an addition funnel. Into the addition funnel was charged the salicyloyl chloride solution from Step 1. The acid chloride was slowly added to the reaction flask at room temperature before the reaction, temperature was increased to 50° C. and held for six hours. The mixture was then cooled and filtered under vacuum to remove pyridine salts. The filtrate was reduced under vacuum before being added to a few mls of saturated sodium bicarbonate solution a and stirred. The heterogeneous solution was then extracted with ether. The organic layer was isolated and extracted three times with water before being dried over magnesium sulfate, filtered and concentrated under reduced pressure to yield the crude product.

The crude products were first vacuum distilled before being further purified by silica gel chromatography. Product confirmation was provided by gas chromatography, gas chromatography/mass spectrometry, 200 MHz proton NMR and FT-IR.

TABLE 4

30 minute incubation, 48 well plate

| Treatment | % Reduction | Std Deviation | T-test |
|---|---|---|---|
| 0.005% Straight Chain TDS | (0.18) | 16.6 | 0.99 |
| 0.01% Straight Chain TDS | 1.3 | 11.9 | 0.91 |
| 0.005% Isotridecyl salicylate | 24.6 | 11.5 | 0.041 |
| 0.01% Isotridecyl salicylate | 48.9 | 8.2 | 0.001 |
| 0.005% Methyl TDS | (11.6) | 7.8 | 0.24 |
| 0.01% Methyl TDS | (16.5) | 5.7 | 0.089 |
| 0.005% Ethyl TDS | (24.5) | 5.5 | 0.029 |
| 0.01% Ethyl TDS | (23.5) | 8.4 | 0.062 |

The results in Table 4 demonstrate that of salicylate esters only isotridecyl salicylate which contained multiple methyl branches was effective in suppressing sebum.

EXAMPLE 5

The sebocyte assay procedure described in Example 2 was repeated with additional branched esters. The results that were obtained are summarized in Table 4. Isotridecyl linoleate and isotridecyl benzoate were synthesised according to the procedure of Example 1, using Exxal® 13 isotridecanol as starting material. The results that were obtained are summarized in Table 5. Phenol Red was used as a positive control.

TABLE 5

20 hour incubation, 48 well plate

| Treatment | % Reduction | P value |
| --- | --- | --- |
| 0.000046% Isotridecyl Linoleate | 57.3 | 0.001 |
| 0.00046% Isotridecyl Linoleate | 50.9 | 0.004 |
| 0.0046% Isotridecyl Linoleate | 44.9 | 0.014 |
| 0.000039% Isotridecyl Benzoate | 36.3 | 0.023 |
| 0.00039% Isotridecyl Benzoate | 52.2 | 0.002 |
| 0.0039% Isotridecyl Benzoate | 41.8 | 0.025 |

It can be seen from the results in Table 5 that branched benzoate and linoleate esters were effective sebum suppressors. When comparing the results in Table 5 to the results in Tables 1 and 2, it can be seen that linoleate and benzoate esters were superior to acetate esters, and that linoleate ester was the most effective.

EXAMPLE 6

This example measured production of procollagen I by fibroblasts in response to treatment with various test compounds.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, NY and used in passages 5–10. Cells were seeded at a density of approximately 7,500/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions). Cells were then grown to confluence for 2 days. At confluence, the medium was removed and cells were washed with serum-free DMEM, and each well dosed with 200 µl of a solution of a test compound in serum-free DMEM. Each dosing was replicated in the total of six wells. Test compounds were used at concentrations indicated in Table 1 below. Control did not contain a test compound. After 24 hours, the test compound solution or the control solution was removed and cells redosed with 100 µl of a solution of a test compound in serum-free DMEM. Test compounds were used at concentrations indicated in Table 1 below. After 24 hours, the test compound solution or the control solution was removed and stored over the weekend at 4° C. with protease inhibitor (Aprotinin from Sigma) in a ratio of aprotinin to water of 1:200. The test compound solution was then diluted in DMEM (approximately 20 µl sample in 200 µl DMEM).

Nitrocellulose membrane and 3 sheets of filter paper were soaked in TRIS buffered saline (TBS, pH 7.3.). BioRad slot blot apparatus (BioRad Labs, CA) was set up with filter paper on bottom, membrane on top, tightened. 100ml TBS was added per well. Vacuum was used to suck wells through membrane. The diluted test compound solution or control was vortexed, then 100 µl was loaded per well and gravity dried. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was washed 3 times for 5 minutes in TBS/0.1%Tween. 3 mL PBS was incubated with 30 µl each of solutions A and B from Vectastain Kit for 30 minutes. The membrane was placed in the resulting solution for 30 minutes in a sealed bag with shaking. The membrane was then removed and washed twice for 5 minutes in TBS/0.1% Tween. The membrane was then stained using the following solution:

12.5 mg 3-amino 9-ethyl carbazole (Sigma)

3.125 (approximately) mL DMF (N,N-dimethylformamide, from Sigma)

21.5 mL 0.2M NaOAc buffer, pH 5.2

12.5 µl $H_2O_2$

The membrane was stained until color developed and the reaction stopped with 2 washes for 10 minutes in tap water. A transparency of the blot was prepared using a color copier. Blot was scanned on Bio-Rad GS-700 Image Analysis densitometer and volume (OD*mm$^2$) of color/slot determined using molecular analysis software. Fold increase was calculated as a ratio of densitometer reading for cells treated with a test compound over control. The results that were obtained are summarized in Tables 6A and 6B.

TABLE 6A

| Test Compound (0.01%) | Average OD Reading | Standard Deviation | p-value (vs. control) | Fold increase over control |
| --- | --- | --- | --- | --- |
| Control-1 | 2.977 | 0.687 | | |
| Exxate ® 600 | 4.324 | 1.027 | 0.023 | 1.5 |
| Exxate ® 700 | 4.434 | 0.974 | 0.013 | 1.5 |
| Exxate ® 800 | 3.620 | 0.711 | 0.142 | 1.2 |
| Control-2 | 3.512 | 0.312 | | |
| Exxate ® 900 | 3.789 | 0.106 | 0.066 | 1.1 |
| Exxate ® 1000 | 3.473 | 0.470 | 0.867 | 1.0 |
| Exxate ® 1200 | 2.829 | 0.792 | 0.077 | 0.8 |
| TGF-b | 6.787 | 0.201 | 1 × 10$^{-9}$ | 1.9 |
| Control-3 | 3.824 | 0.352 | | |
| Exxate ® 1300 | 4.33 | 0.315 | 0.025 | 1.1 |

TGF-b was incorporated as a positive control

It can be seen from the results in Table 6A that methyl-branched acetate esters within the scope of the invention, based on shorter chain alcohols (i.e. less than 9 carbons) were effective in increasing collagen production by fibroblasts.

TABLE 6B

| Test Compound | Average OD Reading | Standard Deviation | p-value (vs. control) | Fold increase over control |
|---|---|---|---|---|
| Control | 1.963 | 0.327 | | |
| TGF-b | 4.099 | 0.486 | $4.4 \times 10^{-6}$ | 2.1 |
| 0.003% Isotridecyl Benzoate | 2.534 | 0.144 | 0.00288 | 1.3 |
| 0.030% Isotridecyl Benzoate | 2.669 | 0.167 | 0.000825 | 1.4 |
| 0.0046% Isotridecyl Linoleate | 2.346 | 0.595 | 0.197222 | 1.2 |
| 0.046% Isotridecyl Linoleate | 2.4585 | 0.412 | 0.04357 | 1.3 |

It can be seen from the results in Table 6B that benzoate and linoleate esters within the scope of the invention increased collagen production by fibroblasts.

EXAMPLE 7

Example shows benefit in enhancing glycosaminoglycan synthesis with novel iso-alcohol esters.

Neonatal human dermal fibroblasts were seeded at a density of approximately 50,000/well in a 12-well plate in a medium containing DMEM (high glucose supplemented with 2 mM L-glutamine, 10% fetal bovine serum, antibiotic and antimycotic solutions). Cells were then grown to confluence for 2 days. At confluence, each well was rinsed in serum-free DMEM and the cells dosed with test compounds (in triplicate) in 750 μL of serum-free DMEM. After 24 hours, this medium was aspirated and the treatment step repeated. After a second 24-hour period, this medium, containing the soluble GAGs, was collected and frozen until analysis.

A positively-charged Zeta Probe membrane was soaked in sterile water and placed into the Dot-Blot Apparatus (both Bio-Rad Labs, Hercules, Calif.). 100 μL of water was applied to each well and pulled through using a vacuum. After thawing, 100 μL of test solution samples or standards (Hyaluronic acid or Chondroitin Sulfate from bovine trachea, Sigma, St. Louis, Mo.) was applied to the membrane and allowed to gravity filter (about 1.5–2 hours). GAGs were now bound to membrane. The membrane was blocked in 3% w/v fatty acid free bovine serum albumin (Sigma) in water for one hour. A dye solution of 0.5% w/v Alcian Blue dye (ICN Biochemicals, Cleveland, Ohio.) in 3% acetic acid, pH approximately 2.3, was made. The membrane was washed twice in distilled water and then stained in the dye solution on a rotary shaker for 15 minutes. The dye was poured off and the membrane destained twice for 15 minutes each time in 3% acetic acid. The membrane was rinsed in water and left to dry overnight. The blot was scanned on Bio-Rad GS-700 Image Analysis Densitometer and volume (OD*mm$^2$) of color/slot determined using molecular analyst software. Fold increase over control was calculated as a ratio of densitometer reading for cells treated with a test compound over control.

TABLE 7

| Test Compound | Average OD Reading | Standard Deviation | p-value (vs. control) | Fold increase over control |
|---|---|---|---|---|
| Control | 0.26 | 0.055 | | |
| TGF-b | 0.86 | 0.16 | $6.2 \times 10^{-6}$ | 3.3 |
| 0.003% Isotridecyl Benozate | 0.22 | 0.044 | 0.17 | 0.8 |
| 0.03% Isotridecyl Benzoate | 0.38 | 0.080 | 0.012 | 1.5 |
| 0.0046% Isotridecyl Linoleate | 0.40 | 0.039 | 0.0007 | 1.5 |
| 0.046% Isotridecyl Linoleate | 0.29 | 0.071 | 0.51 | 1.1 |

It can be seen from the results in Table 7 that benzoate and linoleate esters were effective at enhancing glycosaminoglycan synthesis by fibroblasts.

EXAMPLE 8

Example 8 illustrates topical compositions according to the present invention. The compositions can be processed in conventional manner. They are suitable for cosmetic use. In particular the compositions are suitable for application to oily, wrinkled, rough, aged and/or UV-damaged skin to improve the appearance and the feel thereof as well as for application to healthy skin to prevent or retard deterioration thereof.

| OIL IN WATER EMULSION CREAM | | |
|---|---|---|
| Ingredient | CTFA or Chemical Name | weight % |
| Polawax Regular | Emulsifiable Wax | 5 |
| Exxate ® 12 | isoalcohol ester | 5 |
| Myristyl myristate | Same | 2 |
| Dow Corning 3225 | Cyclomethicone and dimethicone copolyol | 2 |
| Aerosil 200 | Silica | 1 |
| Sepigel 305 | Poyacrylamide and C13–14 isoparaffin and laureth-7 | 0.5 |
| Glycerine microsponges | Methacrylate copolymer with glycerine | 0.5 |
| Brij 58 | ceteth-20 | 0.3 |
| Methyl paraben | Same | 0.2 |
| Germall 115 | Imidazolidinyl urea | 0.2 |
| propyl paraben | Same | 0.15 |
| BHT | butylated hydroxy toluene | 0.05 |
| Water | Same | to 100 |
| Sequesterene Na2 | Disodium EDTA | 0.05 |
| Veegum Ultra | Magnesium aluminum silicate | 0.6 |
| Methyl Paraben | Methyl paraben | 0.15 |
| DC Antifoam Emulsion | Simethicone | 0.01 |
| Butylene Glycol 1,3 | Butylene glycol 1,3 | 3.0 |
| Natrosol 250HHR | Hydroxyethylcellulose | 0.5 |
| Aerosil 200 | Fumed silica | 0.5 |
| Glycerine USP | Glycerine, USP | 2.0 |
| Keltrol 1000 | Xanthan gum | 0.2 |
| Triethanolamine 99% | Triethanolamine | 1.2 |
| Pristerene 4911 | Stearic acid | 3.0 |
| Propylparaben NF | propyl paraben NF | 0.1 |
| Naturechem GMHS | Glyceryl hydrostearate | 1.5 |
| Lanette 18DEO | Stearyl alcohol | 1.5 |
| Exxate ® 13 | isoalcohol ester | 4.0 |
| Protachem ISP | Isostearyl palmitate | 3.0 |
| Hetester FAO | C12–15 alcohols octanoate | 2.0 |
| Silicone Fluid 200(50 cts) | Dimethicone | 1.0 |
| Cholesterol NF | cholesterol NF | 0.5 |
| Sorbitan Stearate | sorbitan stearate | 1.0 |
| Embanox BHT | butylated hydroxytoluene | 0.05 |

-continued

OIL IN WATER EMULSION CREAM

| Ingredient | CTFA or Chemical Name | weight % |
|---|---|---|
| Vitamine E Acetate | tocopheryl acetate | 0.1 |
| MYRJ 59 | PEG-100 stearate | 2.0 |
| Pationic SSL | sodium stearoyl lactylate | 0.5 |
| Alpha-bisabolol | alpha-bisabolol | 0.2 |
| water | Same | to 100 | water-in-oil emulsion

| CTFA or Chemical Name | weight % |
|---|---|
| squalane | 5 |
| macadamia oil | 5 |
| pentaerythritol tetraoctanoate | 15 |
| petrolatum | 5 |
| glyceryl stearate | 3 |
| tocopherol acetate | 0.5 |
| butylated hydroxytoluene | 0.05 |
| methyl paraben | 0.15 |
| propyl paraben | 0.15 |
| sodium citrate | 1 |
| butylene glycol | 2 |
| glycerol | 2 |
| bentone clay | 0.5 |
| disodium EDTA | 0.05 |
| Bofridecyl linoleate | 10 |
| Water | to 100 |
| Glycerin | 1 |
| Tetrasodium EDTA | 0.1 |
| Cetyl alcohol | 1 |
| Stearyl alcohol | 1 |
| Mineral oil | 5 |
| Dimethicone | 1 |
| Dimethiconol | 0.2 |
| Polyquaternium 37 | 2 |
| Steareth-21 | 1 |
| Steareth-2 | 0.5 |
| Isotridecyl benzoate | 1 |
| Cyclomethicone | 0.5 |
| Silica | 0.6 |
| Water | to 100 |
| light mineral oil | 10 |
| Stearoxytrimethylsilane and stearyl alcohol | 5 |
| dimethicone | 2 |
| stearyl stearate | 10 |

-continued water-in-oil emulsion

| CTFA or Chemical Name | weight % |
|---|---|
| quaternium-15 | 3 |
| peg-22 dodecyl glycol copolymer | 1 |
| Sorbitol | 0.5 |
| methyl paraben | 0.2 |
| disodium EDTA | 0.1 |
| butylated hydroxytoluene | 0.1 |
| Exxate ® 7 | 5 |
| Silica | 1 |
| Water | to 100 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin care cosmetic composition comprising:

(i) from about 0.1% to about 10% of a branched chain ester RCOOR', wherein R is selected from the group consisting of $CH_3$, phenyl, and $CH_3(CH_2)_4 CH=CHCH_2CH=CH(CH_2)_7$; and R' is a methyl-branched aliphatic hydrocarbon radical containing a total of at least 6 carbons, provided that if R' contains more than 6 carbon total, the branched ester contains more than one methyl group; and (ii) a cosmetically acceptable vehicle; and further comprising a retinoid.

2. A skin care cosmetic composition comprising:

(i) from about 0.001% to about 50% of a branched chain ester RCOOR', wherein R is $CH_3(CH_2)_4 CH=CHCH_2CH=CH(CH_2)_7$ and R' is a methyl-branched aliphatic hydrocarbon radical containing a total of at least 6 carbons, provided that if R' contains more than 6 carbon total, the branched ester contains more than one methyl group; and (ii) a cosmetically acceptable vehicle.

* * * * *